Figure 1:
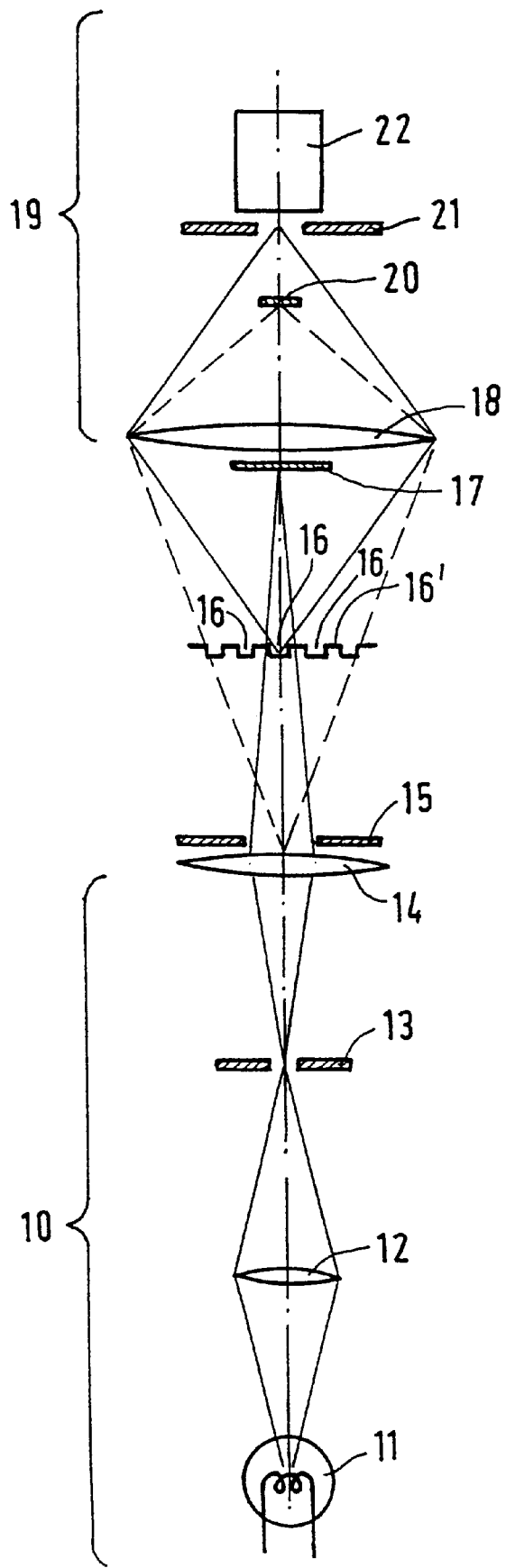

United States Patent

Moore

[11] Patent Number: 6,020,961
[45] Date of Patent: Feb. 1, 2000

[54] NEPHELOMETER

[75] Inventor: Thomas Moore, Jena, Germany

[73] Assignee: Merlin Gesellschaft fuer mikrobiologische Diagnostik mbH, Bornheim-Hersel, Germany

[21] Appl. No.: 09/077,526

[22] PCT Filed: Nov. 28, 1996

[86] PCT No.: PCT/EP96/05254

§ 371 Date: Jul. 29, 1998

§ 102(e) Date: Jul. 29, 1998

[87] PCT Pub. No.: WO97/20199

PCT Pub. Date: Jun. 5, 1997

[30] Foreign Application Priority Data

Nov. 30, 1995 [DE] Germany ............................. 195 44 645
Sep. 13, 1996 [DE] Germany ............................. 196 37 364

[51] Int. Cl.$^7$ .................................................. G01N 21/00
[52] U.S. Cl. ............................................ 356/338; 356/339
[58] Field of Search .................................. 356/335–343; 250/564, 574

[56] References Cited

U.S. PATENT DOCUMENTS 4,679,939  7/1987  Curry et al. ............................. 356/336

FOREIGN PATENT DOCUMENTS 0 226 843  7/1987  European Pat. Off. .
881 877  7/1950  Germany .
926 993  3/1952  Germany .

*Primary Examiner*—Frank G. Font
*Assistant Examiner*—Michael P. Stafira

[57] ABSTRACT

The Nephelometer comprises an illumination device (10) and a detector device (19). By means of the illumination device (10), a sample to be analyzed being arranged in a chamber (16) is illuminated, the scattered light emanating from the sample being detected by the detector device (19). A central shading element (17) arranged in a plane conjugate to the light source (11) of the illumination device (10) is located between the sample chamber (16) and the detector device (19). The detector device (19) further comprises another shading element (20) located in a plane conjugate to the exit opening shutter (15) of the illumination device (10). Direct light from the sample to be analyzed is absorbed by the central shading element (17), while the further shading element (20) absorbs stray light exiting from the exit opening shutter (15) of the illumination device (10) and impinging on the entrance lens arrangement (18) of the detector device (19) without passing through the sample.

10 Claims, 2 Drawing Sheets

NEPHELOMETER

This application claims the benefit under 35 U.S.C. §371 of prior PCT International Application Ser. No. PCT/EP96/05254 which has an International filing date of Nov. 28, 1996 which designated the United States of America, the entire contents of which are hereby incorporated by references.

The invention relates to the arrangement of various optical and optoelectronic assemblies to form a nephelometric measuring device. Thus, the invention relates to the arrangement of various optical and optoelectronic components and assemblies to form an optical measuring channel for measuring the scattered light of samples. In this context, a nephelometric arrangement is presupposed, i.e., only light scattered by the sample in a certain solid angle is measured.

Conventional nephelometers for liquid samples in cuvettes operate as follows:

The sample is filled into a cuvette and is transilluminated by light of small bandwidth and low divergence. The light scattered by the sample is measured by a detector arranged at a right angle to the transillumination direction.

There is a large number of modifications of this principle:

An example is the objective to reduce the influence of the cuvette on the background signal (DE-OS 29 07 000) or to obtain further data by measuring the scattered light in various solid angle ranges, for example 90° and 35° (DE-OS 29 20 276).

Of special interest are arrangements which are also able to measure samples arranged in the form of a matrix, for instance in so-called microtitration plates or on flat transparent supports, e.g. glass plates. Such a system which transilluminates the sample in a vertical direction and which can be equipped with a mechanical movement means for horizontally positioning the samples is described in DE-OS 35 35 652.

The principle of this arrangement consists in the combination of an illumination device transilluminating the sample and a detector device with a detector and a detector optical system with high which concentrates the scattered light onto a detector in this context, the light directly passing through the sample is absorbed by a central shading element in the central zone of the detector optical system.

This arrangement has the disadvantage that the signal is unsatisfactorily high in the case of measurements in the air and in the case of an empty cuvette and that the overall sensitivity is too low.

From DE-OS 24 09 273, an optical arrangement is known for measuring antigen-antibody reactions in which scattered light emanating from a sample is obtained by means of a detector device. The light originating from an illumination device transilluminates a sample behind which a light trap is arranged for absorbing direct light. Within the detector optical system, a black shutter is arranged on the optical axis of the arrangement for shuttering out scattered light originating from shutters arranged between the illumination device and the sample.

The object is to design this arrangement such that the sensitivity of the measuring system is high and free of background signals and the use of multiple open-top vessels is possible. Thus, it is the object of the invention to be able to measure nephelometrically samples arranged in the form of a matrix in open-top vessels with high sensitivity and free from disturbing background signals.

To achieve this object, the invention proposes a nephelometer for optically detecting the scattered light of an illuminated sample, comprising an illumination device (subsequently also called illuminator) for illuminating a sample. The illumination device further comprises a light source, an exit lens assembly (subsequently also called illuminator optical system) and an exit opening shutter (subsequently also called exit pupil) which are arranged, in this order, on a common optical axis originating in the light source. A detector device is provided to detect the scattered light originating from the sample. This detector device comprises a central shading element by means of which the light directly passing through the sample can be absorbed so that it does not impinge on the detector device and especially not on the detector thereof. The detector device further comprises a detector entrance lens arrangement (subsequently also called detector optical system). Furthermore, the detector device comprises a second shading element arranged between the detector entrance lens arrangement and the detector.

According to the invention, the exit opening shutter of the illumination device and the entrance lens arrangement as well as the two shading elements of the detector device are arranged relative to one another such that the central shading element is in a plane optically conjugate to the light source and that the second shading element is in a plane optically conjugate to the exit opening shutter. In other words, the light source is imaged onto the central shading element while the exit opening shutter is imaged onto the second shading element.

It is the object of the second shading element to absorb the light not primarily scattered by the sample. This light is the light which exits from the exit opening shutter of the illumination device, but is diffracted there or scattered within the measuring channel and thus impinges on the detector device, potentially by passing through the sample. This stray light is absorbed by the second shading element, thus does not get onto the detector and thus cannot adulterate the measured result.

In a nephelometer according to the invention, the sample is arranged between the exit opening shutter of the illumination device and the central shading element of the detector device. In this context, the sample is imaged onto the detector, i.e., the sample and the detector are in planes conjugate to each other. Furthermore, the distance between the exit opening shutter of the illumination device and the sample should be sufficiently large. If the exit opening shutter, for example, were to coincide with the sample, all the stray light would be trapped by the detector. In the case of a sufficient distance between the exit opening shutter and the sample, it is practical, in order to trap all the stray light, if possible, to arrange the second shading element as close as possible to the focus of the detector entrance lens assembly. The second shading element is located between this focus and the detector.

The central shading element should be as small as possible, so that even light from the sample scattered in the smallest angle to the optical axis reaches the detector. Ideally, only that light should be shaded by the shading element which travels on the optical axis and passes directly through the sample (direct light beam). As the shading element is in the plane conjugate to the light source, the light source thus would have to be small. This, in turn, is advantageously achieved by means of a laser instead of, for example, a conventional light source with a heating coil.

Further advantageous embodiments of the invention are described in the subclaims.

An exemplary embodiment of the invention will now be described in greater detail with reference to the drawings.

Figure 2:
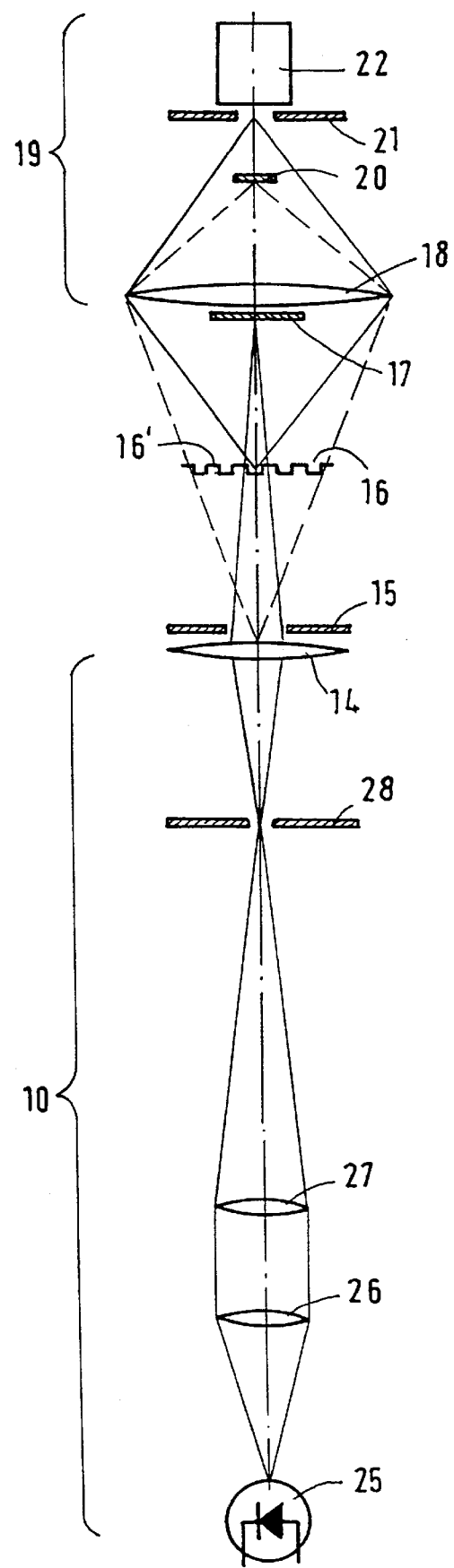

FIG. 1 shows the optical path of the nephelometric measuring arrangement with a conventional light source and FIG. 2 shows the optical path of the nephelometric measuring arrangement with a laser light source.

In FIG. 1, the optical path is represented beginning with the illumination device 10 comprising a conventional light source 11, e.g. a halogen lamp, and an illuminator assembly consisting of the illuminator lens 12 and the exit lens 14, a field stop 13 arranged therebetween and an exit opening shutter 15. The light source 11 is imaged into the field stop 13. The field stop 13 is imaged onto a central shading element 17 by the exit lens 14. In this context, the illumination device aperture is limited by the exit opening shutter 15 thereof.

The image of the light source 11 or the field shutter 13 on the central shading element 17 has a typical diameter of some tenths of a millimeter up to a few millimeters.

The light of the illumination device 10 exiting through the exit opening shutter 15 passes through the sample liquid in an open-top chamber 16 of a microtitration plate 16'. The microtitration plate 16' is displaceable in the plane vertical to the optical path. The light passing through the sample liquid gets onto the entrance lens 18 of a detector device 19 arranged opposite the illumination device 10 on the optical path (optical axis).

In the detector device 19, the sample is imaged into a detector shutter 21 arranged immediately in front of the detector 22 by means of the entrance lens of the detector device, whereby the light gets onto the detector 22.

The exit opening shutter 15 of the illumination device 10 is imaged onto another shading element 20 by means of the detector entrance lens 18. Thereby, (stray) light coming directly from the illumination device 10 without having passed through the sample is absorbed by the shading element 20 and cannot adulterate the measuring results. Thus, the detector 22 exclusively receives (scattered) light passing through the sample, as direct light is absorbed by the central shading element 17 and stray light is absorbed by the further shading element 20.

In an alternative arrangement according to FIG. 2, in which similar components as in the arrangement according to FIG. 1 are referred to by the same reference numerals, the light source is selected to be a laser 25, e.g. a semiconductor laser. This is associated with a collimator lens 26. The laser collimator formed thus produces a laser radiation of a low divergence impinging on an objective lens 27 on the optical axis having a longer focus than the laser collimator lens 26 so that an enlarged image of the laser light source 25 in the pinhole stop 28 of the illumination device 10 is formed. The pinhole stop 28 works as a spatial filter together with the objective lens 27. The diameter of such pinhole stops in the application as a spatial filter is in the area of a few hundredth of a millimeter. The exit lens 14 of the illumination device now images this pinhole stop 28 on the central shading element 17. In this context, it is possible to put into practice comparatively large imaging scales and therefore distances between the exit opening shutter 15 of the illumination device 10 and the central shading element 17. This especially applies to shading elements smaller than those possible in the case of conventional illumination. As in FIG. 1, the exit opening shutter 15 of the illumination device 10 is imaged on the further shading element 20 arranged between the detector 22 and the entrance lens 18 close to the focus of the illumination device. As in the arrangement of FIG. 1, it is also true in the case of FIG. 2 that the central shading element 17 is arranged immediately in front of the entrance lens 18 of the detector device 19.

In the case of the two exemplary embodiments described above, the light source of the illumination device is imaged directly onto a central shading element with good absorbing features of the detector optical system high apertured of the detector device, while the detector optical system images the exit opening shutter onto a further shading element, likewise with good absorbing features, in the image area of the detector optical system.

This is achieved by means of an arrangement for the optical guiding of beams in a light or beam measuring device which consists of a unit for illuminating the sample and a detector unit for measuring the radiation emitted or re-emitted by the sample such that the light source of the illumination device is imaged onto an absorbing element forming part of the detector device and the exit opening shutter of the illumination device is imaged onto a further absorbing element arranged on the side of the image and also forming part of the detector device.

As is known, the forward scattering of many samples is especially strong so that it is suitable to minimize the central shading of the detector optical system. This is achieved by the light source of the illumination device or a shutter conjugate thereto being imaged onto this shading element. Of course it is still important that this shading element absorbs the impinging light very well. Thus, it is suitable to use black mat varnish for this purpose, to form the shading element as a funnel-shaped light trap or to use totally absorbent dielectric layers or extremely well antireflected absorbing glasses in the case of a strictly monochromatic light radiation.

The central shading element of the detector device can be selected to be extremely small if a laser is used as a light source (FIG. 2).

In the case of a conventional light source, this arrangement is advantageous as long as the image diameter remains smaller than the aperture cone diameter.

Usually, the influence of the background illumination increases when the central shading element is reduced in size. However, if the illumination device is arranged such that the exit opening shutter thereof is imaged by the detector optical system onto a screen, i.e. a further shading element in the image area of the detector optical system, the content of the background signal is reduced. This further shading element is located in the image, created by the detector optical system, of the exit opening shutter of the illumination device and thus between the focus of the detector optical system and the detector shutter arranged immediately in front of the detector. It is advantageous if the aperture shutter image of the illumination device is close to the focus of the detector optical system. The strongly reduced image of the aperture shutter only requires a very small shading element the diameter of which does not reduce the aperture cone impinging on the detector and thus does not reduce the sensitivity.

The arrangement can also be described such that the exit opening shutter of the illumination device has to be located far to the outside of the depth of focus range of the detector optical system, which is achieved by the two images being linked such that the back focus between the exit opening shutter of the illumination device and the entrance lens arrangement of the detector device is maximized and thus the pixel of the exit opening shutter of the illumination device approximates the focus of the detector opening. Even in this case, use of a laser is advantageous, as such a long back focus is possible without problems in the case of a small image of the light source in the shading plane when the luminance is high.

In the case of a conventional light source, for example a halogen lamp, it is advantageous to delimit sharply the image thereof in the shading plane by a shutter located within the illumination device (FIG. 1). The intermediate image necessary for this purpose also contributes to the reduction of the background signal.

If a laser is used as a light source, this arrangement exactly corresponds to a spatial filter, which leads to an extreme reduction of the background signal, thus giving the laser a further advantage (FIG. 2).

I claim:

1. Nephelometer for optically detecting scattered light from an illuminated sample, comprising an illumination device (10) for illuminating a sample, the illumination device (10) comprising a light source (11; 21), an exit lens arrangement (14) and an exit opening shutter (15) arranged, in this order, on a common optical axis originating in the light source (11; 21) and a detector device (19) for detecting the scattered light from the sample, the detector device (19) comprising a central shading element (17) for absorbing light directly passing through the sample from the light source (11; 21)and impinging on the detector device (19), a detector entrance lens arrangement (18), a second shading element (20) for absorbing light from the light source (11; 21) directly impinging on the detector device (19) from the exit opening shutter (15) of the illumination means (10) and a detector (22), which are arranged, in this order, on the optical axis, the exit opening shutter (15) of the illumination device (10) and the entrance lens arrangement (18) as well as the two shading elements (17, 20) of the detector device (19) being arranged such that the central shading element (17) is in a plane conjugate to the light source (11; 21) and the second shading element (20) is in a plane conjugate to the exit opening shutter (15).

2. Nephelometer according to claim 1, characterized in that the second shading element (20) is arranged between the detector entrance lens arrangement (18) and the detector (22), as close as possible to the focus of the detector entrance lens arrangement (18).

3. Nephelometer according to claim 1 or 2, characterized in that the central shading element (17) is positioned immediately in front of the detector entrance lens arrangement (18).

4. Nephelometer according to claim 1, characterized in that an internal lens arrangement (12; 22, 27) and a field stop (13; 28) are arranged between the light source (11) and the exit lens arrangement (14) of the illumination device (10), the field stop (53) being arranged in a plane conjugate to the light source (11).

5. Nephelometer according to claim 1, characterized in that the light source (21) is a laser.

6. Nephelometer according to claim 5, characterized in that the internal lens arrangement comprises a collimator lens (22) and an objective lens (27) and the field stop is formed as a pinhole stop.

7. Nephelometer according to claim 2, characterized in that an internal lens arrangement (12; 22, 27) and a field stop (13; 28) are arranged between the light source (11) and the exit lens arrangement (14) of the illumination device (10), the field stop (53) being in a plane conjugate to the light source (11).

8. Nephelometer according to claim 3, characterized in that an internal lens arrangement (12; 22, 27) and a field stop (13; 28) are arranged between the light source (11) and the exit lens arrangement (14) of the illumination device (10), the field stop (53) being arranged in a plane conjugate to the light source (11).

9. Nephelometer according to claim 2, characterized in that the light source (21) is a laser.

10. Nephelometer according to claim 3, characterized in that the light source (21) is a laser.

* * * * *